United States Patent [19]
Richards et al.

[11] Patent Number: 5,439,893
[45] Date of Patent: Aug. 8, 1995

[54] METHODS FOR THE TREATMENT AND PREVENTION OF DIARRHEA

[75] Inventors: Geoffrey N. Richards; Carolyn E. Campbell, both of Missoula, Mont.

[73] Assignee: University of Montana, Missoula, Mont.

[21] Appl. No.: 66,843

[22] Filed: May 26, 1993

[51] Int. Cl.⁶ .................... A61K 31/70; C08B 37/00
[52] U.S. Cl. ........................ 514/53; 514/54; 514/61; 514/867; 424/439; 424/442; 426/71; 426/650; 426/658; 426/660; 426/801
[58] Field of Search ............ 514/53, 54, 61, 867; 424/439, 442; 426/71, 650, 658, 660, 801

[56] References Cited

U.S. PATENT DOCUMENTS

| | | | |
|---|---|---|---|
| 4,622,341 | 11/1986 | Szatloczky et al. | 514/648 |
| 4,762,822 | 8/1988 | Ettinger | 514/25 |
| 4,927,811 | 5/1990 | Quarles | 514/23 |
| 4,963,384 | 10/1990 | Heine et al. | 426/580 |
| 4,994,442 | 2/1991 | Gil et al. | 514/25 |
| 5,013,569 | 5/1991 | Rubin | 426/585 |
| 5,021,245 | 6/1991 | Borschel et al. | 426/2 |
| 5,071,653 | 12/1991 | Kakuda et al. | 424/195.1 |
| 5,206,355 | 4/1993 | Richards et al. | 536/4.1 |
| 5,294,546 | 3/1994 | Dombou et al. | 435/101 |

*Primary Examiner*—Ronald W. Griffin
*Attorney, Agent, or Firm*—Lowe, Price, LeBlanc & Becker

[57] ABSTRACT

The present invention relates to a method for the treatment and prevention of diarrhea comprising administering to humans a sugar selected from the group consisting of a caramel composition comprising a high content of fructose oligosaccharides, termed sucrose thermal oligosaccharides (STO), a composition comprising sucrose thermal kestoses, and fructoglucan polymers. The sugars are a natural product and greatly speed recovery from diarrhea and reduce the recurrence of diarrhea.

16 Claims, No Drawings

METHODS FOR THE TREATMENT AND PREVENTION OF DIARRHEA

TECHNICAL FIELD

The present invention relates to a method for the treatment and prevention of diarrhea comprising administering to humans a sugar selected from the group consisting of a caramel composition comprising a high content of fructose oligosaccharides, termed sucrose thermal oligosaccharides (STO), a food composition comprising sucrose thermal kestoses, and a food composition comprising fructoglucan polymers.

BACKGROUND OF THE INVENTION

Millions of children, adults and infants in less developed nations are born into and live in an environment that is extremely unsanitary. Even in urban areas, roads in low income neighborhoods are frequently unpaved and fecal material from humans and animals is in the air and water storage tanks. Many households have no sanitary latrine facilities. Electricity is frequently unavailable and when it is, families often cannot afford a refrigerator. Households must frequently fetch water from community water faucets at substantial distances. In some communities, there is no piped water at all and residents must rely on tanker trucks to fill drums located outside their shacks. These outside water storage drums are exposed to dirt, dust and many forms of bacteria.

Many families cannot afford the fuel needed to boil drinking water. Thus, unboiled, contaminated water is often used to prepare family meals, infant formula or other baby food. Consequently, the food becomes a vehicle for pathogenic bacteria to colonize the adult, child or infant gut increasing the risk of diarrhea and other disease. If the water is boiled but the prepared food or infant formula remains unrefrigerated for several hours before consumption, it can be colonized by bacteria prior to its consumption.

Pathogenic challenges to the gastrointestinal (GI) tracts of infants, young children and adults, particularly aged adults in low income families in less developed nations are frequent and intense.

The human infant has an immature immune system which does not become fully functional until 6-20 months of age. This deficit is biologically compensated for by the fact that human breast milk provides immunity in the form of antibodies, macrophages, complement and a whole host of other immunological factors that assist the infant GI tract in coping with viral and bacterial hazards in the environment. Human milk also contains lysozyme, a bactericidal enzyme active in the infant GI tract. In addition to protecting the GI tract from infection, human milk also often contains antibodies to systemic (non-GI tract) infections such as respiratory rotaviruses, poliomyelitis and measles.

In addition to antibacterial and antiviral factors, human milk has a chemical, which has been termed the "bifidus factor", which stimulates the intestinal growth of the protective bifidus bacteria, at the expense of competing bacteria, many of which are pathogenic. The bifidus bacteria is a benign microorganism and when it becomes a principal inhabitant of the colon, pathogens are less able to multiply rapidly enough to cause disease.

It has been shown that the greater the frequency of breast feeding, the greater the protection from diarrheal disease. Infants who receive infrequent daily breast feedings, have little protection from such disease compared to infants who receive ad lib breast milk. The bifidus factor as well as the immunity in human milk both play a role in this protective process.

Many efforts are underway around the world to encourage exclusive breast feeding. However, the realities of economic life often mitigate against this, even for those women who would prefer to exclusively breast feed. In the absence of workplace day care, working women in rich and poor countries alike find it virtually impossible to exclusively breast feed.

To date, no simple remedy has been found that could effectively prevent diarrhea in both young children and non-exclusively breast fed infants in the less developed nations. Improved sanitation and hygiene, while desirable from a public health standpoint, are often economically unfeasible in poor nations, particularly given the very rapid growth of squatter communities in large urban centers throughout the developing world.

In addition to young children and infants, adults frequently encounter diarrhea, and the problem may be particularly dangerous for aged adults. Although adults have a more developed immune system more capable of protecting the host from pathogenic attacks, immunocompromised adults, and even healthy adults, are frequently subjected to attacks of diarrhea due principally to the ingestion of contaminated water or food.

Even short periods of diarrhea significantly alter the intestinal absorption of ingested food and liquids in adults, threatening the health of the adult. At the very least, acute diarrhea is a troubling and inconvenient illness. Persistent and chronic diarrhea are more dangerous, since these conditions often result in malnutrition and an increasingly weakened immune system, permitting the host to be invaded by other opportunistic infections. With the elderly as well as young children and infants, diarrhea can be life threatening.

Diarrhea is also expensive to nations and families. The cost of treating diarrhea at a children's hospital (Hospital Infantil Federico Gomez) in Mexico City was recently investigated and it was found that 11% of emergency outpatients and 7.5% of inpatients were diagnosed as having diarrhea.

Caramels are confectionery products obtained by heating glucose, sucrose or other reducing sugars. The time generally required to achieve caramelization is several hours, typically from 3 to 9 hours. The composition of caramels has been studied previously and caramels prepared from sucrose have been shown to contain small amounts of oligosaccharides, predominantly glucose disaccharides.

Recently, a new type of caramel containing a high content of fructose oligosaccharides, termed sucrose thermal oligosaccharides (STO), has been prepared and is described in U.S. patent application No. 07/983,446 filed Dec. 12, 1992, which is hereby incorporated by reference in its entirety.

The sucrose thermal oligosaccharide (STO) caramel of U.S. patent application No. 07/983,446 is prepared by milling sucrose and an organic acid in a ball mill for approximately 0.5 to 4 hours, heating to a temperature of 130°–160° C. for 0.5 to 15 minutes and cooling quickly to produce the sucrose thermal oligosaccharide (STO) caramel product. The caramel contains an unusually high content of fructose oligosaccharides.

Further, two new types of sugar compositions have been recently prepared by the thermolysis of amorphous sucrose under selected conditions for each reaction. In one aspect, kestoses containing fructose moieties are produced by the thermal reaction of amorphous sucrose in the presence of an acid catalyst at a temperature of 80° to 100° C. The product comprises a mixture of sucrose thermal kestoses. In a second aspect, amorphous sucrose is polymerized in admixture with an acid catalyst at temperatures of 125°-175° C. to produce a fructoglucan polymer. The process and final products are set forth in U.S. Pat. No. 5,206,355 issued Apr. 27, 1993, which is hereby incorporated by reference in its entirety.

According to the present invention it has been unexpectedly discovered that STO caramels prepared according to U.S. application Ser. No. 07/983,446 and sucrose thermal kestoses and fructoglucan polymers prepared according to U.S. Pat. No. 5,206,355, significantly prevent the occurrence and reoccurrence of diarrhea in humans.

SUMMARY OF THE INVENTION

It is accordingly an object of the present invention to provide a method for the treatment and prevention of diarrhea comprising administering to a human a sugar selected from the group consisting of a caramel product having a high content of fructose oligosaccharides, termed sucrose thermal oligosaccharides (STO), a sugar composition comprising sucrose thermal kestoses, and a sugar composition comprising fructoglucan polymers.

It is a further object of the present invention to provide a method for improving human health by administering a sugar composition selected from the group consisting of a caramel product having a high content of fructose oligosaccharides (STO caramel), a composition comprising sucrose thermal kestoses and a composition comprising a fructoglucan polymer.

It is a further object of the present invention to provide a method of preparing an improved infant formula comprising at least one sugar composition selected from the group consisting of STO caramel, sucrose thermal kestoses and fructoglucan polymers.

It is a further object of the present invention to provide an improved infant formula comprising at least one sugar selected from the group consisting of STO caramel, sucrose thermal kestoses and fructoglucan polymers.

DETAILED DESCRIPTION OF THE INVENTION

According to the present invention, it has been unexpectedly found that it is possible to greatly treat and prevent diarrhea in humans, thereby increasing human health, by administering at least one sugar selected from the group consisting of a caramel having a high content of fructose oligosaccharides (STO caramel), sucrose thermal kestoses and fructoglucan polymers.

STO caramel, sucrose thermal kestoses and fructoglucan polymers are sugars and do not contain harmful chemicals. They stimulate the body to recover rapidly from diarrhea in a more natural fashion than through the use of drugs or stomach coatings which may have harmful or even toxic side effects. Thus, the method according to the present invention represents a significant achievement in the art of diarrhea medicaments.

STO is basically caramel made under tightly controlled conditions of temperature and humidity. In the absence of water, a small amount of citric acid acts catalytically to induce polymerization so that a disaccharide, sucrose, is transformed into various oligosaccharides consisting of mostly trioses and tetroses.

The STO caramel is prepared according to U.S. patent application Ser. No. 07/938,446. The process includes mixing sucrose and an organic acid in a ball mill for approximately 0.5 to 4 hours, heating to a temperature of 130°-160° C. for 0.5 to 15 minutes and cooling quickly to produce the STO caramel product.

The STO caramel contains at least about 20% fructose oligosaccharides. These fructose oligosaccharides have a DP of 3-10. Accordingly, a STO caramel comprising at least 20% fructose oligosaccharides having a DP of 3-10 may be administered. Other major components of the STO caramel include glucose, fructose, sucrose and kestoses.

The range of contents of the major components of the STO caramel is 30-55% glucose and fructose; 5-15% sucrose; 5-20% kestoses; and 20-50% fructose oligosaccharides having a DP of about 3-10.

In addition, it has been discovered that sucrose thermal kestoses and fructoglucan polymers may be administered to humans according to the present invention for the prevention and treatment of diarrhea. Sucrose thermal kestoses and fructoglucan polymers may be prepared according to U.S. Pat. No. 5,206,355. The process for producing the sucrose thermal kestoses comprises reacting amorphous sucrose with an acid catalyst at a temperature of 80° to 110° C. Amorphous sucrose is defined as sucrose which has the chemical structure of sucrose and substantially no crystalline X-ray diffraction pattern.

The chemical formula of the starting sucrose and the products produced in accordance with the process may be described by the following formula

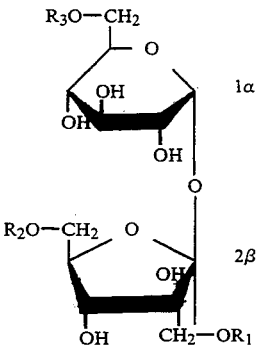

(a) Sucrose, $R_1=R_2=R_3=H$;
(b) 1-kestose, $R_1=\beta$-D-fructofuranosyl, $R_2=R_3=H$;
(c) Iso-1-kestose, $R_1=\alpha$-D fructofuranosyl, $R_2=R_3=H$
(d) 6-kestose, $R_2=\alpha$-D-fructofuranosyl, $R_1=R_3=H$
(e) Iso-6-kestose, $R_2=\alpha$-D-fructofuranosyl, $R_1=R_3=H$
(f) Neokestose, $R_3=\beta$-D-fructofuranosyl, $R_1=R_2=H$.
(g) Iso-neokestose, $R_3=\alpha$-D-fructofuranosyl, $R_1=R_2=H$.

The process for preparing the fructoglucan polymer comprises reacting amorphous sucrose in admixture with an acid catalyst at temperature of 125°-175° C. for a period ranging from about eighty minutes up to two days. The fructoglucan polymer is a highly branched material similar to polydextrose; however, both fructose and glucose occur in the fructoglucan polymers.

The molecular weight of the polymer produced according to the present invention ranges from 2,000 to 10,000 Dalton and has an average of 20 sugar units. The polymer may be characterized as having a glucose to fructose ratio of 1.3:1 up to 2:1, preferably 1.3:1 up to 1.7:1 with a preferred average ratio of 1.66:1.

STO caramels, sucrose thermal kestoses and fructoglucan polymers are not toxic because they are not absorbed, just as the raffinose in beans and other carbohydrate components of fiber are not absorbed. The human gut cannot absorb oligosaccharides until they are digested into monosaccharides. If the oligosaccharides contain chemical bond configurations for which the digestive system has no appropriate enzymes to break those bonds (like the beta linkages between glucose residues in cellulose), they remain unchanged in the GI tract. Colonic microorganisms have a greater variety of digestive enzymes and can often break these unusual linkages.

It has been hypothesized that bifido bacteria, when compared to other colonic microbes, have an abundance of a rare enzyme that allows them to readily digest STO caramel, sucrose thermal kestoses and fructoglucan polymers. Once digested into its monosaccharide components, the released glucose and fructose monosaccharides are absorbed into and metabolized by these bacteria. Bifido bacteria further improve their competitive advantage vis-a-vis other microbes by metabolizing the monosaccharides into acidic by-products which many intestinal pathogens cannot tolerate. Thus, bifido bacteria proliferate and the number of 'acidophobic' bacteria, including most pathogens, decreases.

Therefore, the method of treatment stimulates the body naturally to defend against harmful pathogens. Expensive and possibly harmful drugs with dangerous side effects are not necessary.

According to the present invention, it has been surprisingly discovered that sugars selected from the group consisting of STO caramel, sucrose thermal kestoses and fructoglucan polymers can stimulate the proliferation of bifidus bacteria, in a way analogous to that of human breast milk, providing a method of decreasing both the morbidity and the primary and secondary mortality associated with diarrhea in infants, adults and young children.

Thus, the present invention provides improvements in savings due to fewer admissions to hospitals, lowered mortality rates, less growth retardation, more efficient utilization of food, etc, and will also save families the grief of having to cope with a seriously ill child or adult, or worse, the death of the child or adult since diarrhea can.

According to the present invention, the STO caramel, sucrose thermal kestoses or fructoglucan polymers are administered to humans by any oral method. When the sugars are administered to infants, it is preferable to administer the STO caramel, sucrose thermal kestoses or fructoglucan polymers in the baby infant formula or baby food for convenience, but any other method of administration may be used.

The STO caramel, sucrose thermal kestoses or fructoglucan polymer may be dissolved in water or encapsulated in a sustained release pill which is administered orally. Any other administration means may be used, but it is important that the sugar be administered orally in order to achieve the benefits of treatment and prevention of diarrhea.

The range of contents of the major components of STO caramel is 30–55% glucose and fructose; 5–15% sucrose; 5–20% kestoses; and 20–50% fructose oligosaccharides having a DP of about 3–10. Thus, the STO caramel contains approximately 50% active ingredients and about 50% glucose.

The sucrose thermal kestoses prepared according to the low temperature method described in U.S. Pat. No. 5,206,355 comprise seven distinctly different sugars including sucrose, 1-kestose, 6-kestose, neokestose, iso-1-kestose, iso-6-kestose and iso-neokestose. Sucrose is the starting material. It is believed that the remaining sugars comprising the kestoses comprise the active ingredients which are useful for the prevention and treatment of diarrhea. It is believed that approximately 20% of the reaction product comprises active ingredient.

The fructoglucan polymers prepared according to the high temperature reaction are described in U.S. Pat. No. 5,206,355. As set forth therein, the reaction product comprises glucose oligosaccharides and fructose oligosaccharides as well as glucose-fructose oligosaccharides. It is believed that these oligosaccharides comprise the active ingredients which are useful for the prevention and treatment of diarrhea. These oligosaccharides are produced during the high temperature thermolysis in yields of about 60%.

For the treatment of infants, it is preferred that the infants consume approximately 0.50 to 5.0 grams per day of STO caramel, sucrose thermal kestoses or fructoglucan polymer, depending on the infant size and the severity of the diarrhea. More preferably, 1.0 to 3.0 grams per day of the sugars are administered. Generally, it is preferred to administer 2.0 grams per day to infants which are 6 to 11 months of age, 2.5 grams per day for infants which are 12 to 17 months of age, and 3.0 grams per day or more to infants who are greater than or equal to 18 months of age.

For infant health maintenance, lesser amounts may be administered. Accordingly, depending on the age and size of the infant, it is preferred that the infants consume approximately 0.05 to 3.0 grams per day of STO caramel, sucrose thermal kestoses or fructoglucan polymer.

Conveniently, the sugars may be added to baby food or baby infant formula. Thus, the STO caramel, sucrose thermal kestoses or fructoglucan polymer may be added to baby cereals such as rice and oatmeal cereals. Further, the sugars may be added to baby juices, baby foods such as creamed ham, creamed spinach, corn, apple sauce or other meat, vegetable and fruit baby foods. The sugars may also be used to prepare toddler biscuits.

For younger babies, and in particular infants who are not eating solid food, especially infants who are not breast feeding, the sugars are conveniently added to infant baby formula. Baby formula comprises various milk products preferably supplemented with protein and other nutrients. Baby formula generally comprises non-fat milk with additives such as lactose or sucrose or both, protein supplements, vegetable oils, corn syrup solids, mono- and diglycerides, soy lecithin and carrageenan. The formula may be either in powder or liquid form.

Infants consume approximately 12 to 35 ounces of infant formula per day, depending on the age and size of the infant. Accordingly, the sugar may be administered gradually throughout the day, or administered in a concentrated dose in one feeding.

Therefore, the sugar selected from the group consisting of STO caramel, sucrose thermal kestoses and fructoglucan polymers may be admixed with infant formula in any amount ranging from about 0.01% to about 99.9%. If the sugar is to be administered in a single bottle feeding, the STO caramel, sucrose thermal kestoses or fructoglucan polymer may be mixed with the formula in an amount ranging from about 1.0% to 50.0%, and more preferably about 15.0% to 30.0%. If the sugar is to be administered throughout the day in continuous feedings, the STO caramel, sucrose thermal kestoses or fructoglucan polymer may be admixed with the formula in an amount of about 0.1% to 10.0%, and more preferably about 0.5% to about 5.0%.

Accordingly, the present invention also comprises a method of preparing an improved infant formula and the infant formula prepared thereby. The improved infant formula comprises conventional infant formula which is mixed with at least one sugar selected from the group consisting of STO caramel, sucrose thermal kestoses or fructoglucan polymers in an amount ranging from about 0.01% to 99.9%. For single dose treatments, the infant formula may comprise the sugars in an amount ranging from about 1.0 to 50.0% or more preferably about 15.0 to 30.0%. For continuous dose treatments, the sugar may be present in the infant formula in an amount ranging from about 0.1 to 10.0%, and more preferably about 0.5 to 5.0%.

If the STO caramel, sucrose thermal kestoses or fructoglucan polymers are to be administered to a child or adult, it is administered on the basis of the human's age, health, food intake and size. Generally, it is preferred that the child or adult receive approximately 2 grams per 6-8 kg of body weight. Thus, the child or adult should be administered approximately 2 grams for a young child weighing approximately 30 pounds, to about 20 grams for a large adult. Dosage amounts may be lowered to about 1 grams per day or less if the STO caramel, sucrose thermal kestoses or fructoglucan polymers are administered on a preventive basis rather than a curative one.

It is to be understood that the above prescribed treatment regimens are based on the fact that the unpurified STO caramel and fructoglucan polymers contain approximately 50% active ingredient and the sucrose thermal kestoses contain about 20% active ingredient. The active ingredients may be purified from the sucrose starting material and the non-active sugar by-products if desired. If so, the treatment doses should be adjusted to accommodate the purified form of the sugars. However, it is more convenient to administer the sugars in a non-purified form in order to lower the cost of the method of treating and preventing diarrhea as set forth according to the present invention.

The sugars may be administered to the adult or young child by any method as long as the sugar is orally ingested. Thus, the STO caramel, sucrose thermal kestoses or fructoglucan polymer may be administered alone without any supplements or conveniently dissolved in water, formulated in lozenges, mixed with any food product, formulated into any food product, etc. Any other administration means may be used as long as the sugars are ingested into the gastrointestinal tract in order to prevent and treat diarrhea. It is contemplated that the sugars may be administered via feeding tubes inserted orally or transperitoneally directly into the stomach or jejunum for more seriously ill patients.

With these objectives in mind, the following examples are set forth to demonstrate the invention.

EXAMPLE 1

Ten human infants suffering from diarrhea and ranging from six months old to 11 months of age are selected. None of these infants are fed human breast milk. Five of the infants receive two grams of STO caramel in water per day and five receive two grams of pure glucose as a placebo per day. The STO caramel or pure glucose is mixed in several cc's of sterile water as a concentrated dosage form. The study is conducted for one month.

The five infants receiving STO caramel recover from the diarrhea in a shorter time period than the five infants receiving the placebo. None of the five infants receiving the STO caramel experience an additional attack of diarrhea, in contrast to the control group.

EXAMPLE 2

Fifteen human infants suffering from reoccurring or 'chronic' diarrhea and ranging from 12-17 months of age are selected. During the study, none of the infants receive any breast milk. Seven of the infants receive 4.5 grams of sucrose thermal kestoses admixed with the infant formula and the remaining eight receive 2.5 grams of pure glucose as a placebo. The study is conducted for one month.

The eight infants receiving sucrose thermal kestoses recover from their diarrhea more quickly and have a greater tendency to remain healthy. In contrast, the seven placebo infants show no change and exhibit extended periods of diarrhea and recurring diarrhea.

EXAMPLE 3

Ten elderly male adults suffering from diarrhea are selected. Except for the diarrhea, all ten report that they do not have any other medical problems. Five of the adults receive 16 grams of fructoglucan polymer per day for one week. The other five do not receive any fructoglucan polymer. The five adults receiving the fructoglucan polymer recover faster from the diarrhea and overall report a greater feeling of wellness than the control group.

While various embodiments of the present invention have been described in detail, it is apparent the modifications and adaptations of these embodiments will occur to those skilled in the art. However, it is to be expressly understood that such modifications and adaptations are within the scope of the present invention, as set forth in the following claims.

We claim:

1. A method for the treatment or prevention of diarrhea, said method comprising orally administering to a human, in an effective amount at least one sugar selected from the group consisting of a caramel having a high content of fructose oligosaccharides, sucrose thermal kestoses and fructoglucan polymers.

2. The method according to claim 1, wherein said caramel contains at least about 20% of fructose oligosaccharides having a DP of 3-10.

3. The method according to claim 1, wherein said caramel comprises about 30-55% glucose and fructose; about 5-15% sucrose; about 5-20% kestoses; and about 20-50% fructose oligosaccharides having a DP of about 3-10.

4. The method according to claim 1, wherein said thermal kestoses comprise at least one material selected from the group consisting of iso-1-kestose, iso-6-kestose and iso-neokestose.

5. The method according to claim 1, wherein said thermal kestoses are the product of heating amorphous sucrose and about 0.2 to 5 wt.% of an acid catalyst.

6. The method according to claim 1, wherein said thermal kestoses comprise a mixture containing 1-kestose, 6-kestose, neokestose, iso-1-kestose, iso-6-kestose and iso-neokestose.

7. The method according to claim 1, wherein said fructoglucan polymers include glucose oligosaccharides and fructose oligosaccharides and glucose-fructose oligosaccharides.

8. The method according to claim 1, wherein said sugar is mixed with a food product in an amount of 0.01% to 99.9%, and said food product is administered to said human.

9. The method according to claim 8, wherein said food product comprises an infant formula.

10. The method according to claim 9, wherein said sugar is present in said infant formula in an amount ranging from about 1.0 to 50.0%.

11. A method of preparing an improved infant formula comprising admixing infant formula with an effective amount of at least one sugar selected from the group consisting of a caramel having a high content of fructose oligosaccharides, sucrose thermal kestoses and fructoglucan polymers.

12. The method according to claim 11, wherein said sugar is admixed with said infant formula in an amount ranging from about 0.01% to 99.9%.

13. An improved infant formula prepared according to claim 11.

14. Treating or preventing diarrhea in a human subject by a method comprising orally administering to said human an effective amount of at least one sugar selected from the group consisting of fructose oligosaccharides, sucrose thermal kestoses and fructoglucan polymers so as to stimulate the proliferation of bifido bacteria and decrease the population of pathogenic bacteria in the subject's colon.

15. The method according to claim 14 wherein the human subject is an infant and the effective amount of said sugar administered is 2.0 to 3.0 grams per day, the particular amount depending upon the infant's age.

16. The method according to claim 15 wherein the sugar is administered in admixture with baby food or baby formula.

\* \* \* \* \*